United States Patent
Emmons et al.

(10) Patent No.: US 10,922,944 B2
(45) Date of Patent: Feb. 16, 2021

(54) METHODS AND SYSTEMS FOR EARLY DETECTION OF CAREGIVER CONCERN ABOUT A CARE RECIPIENT, POSSIBLE CAREGIVER IMPAIRMENT, OR BOTH

(71) Applicant: Hill-Rom Services, Inc., Batesville, IN (US)

(72) Inventors: Kirsten M. Emmons, Batesville, IN (US); David Lance Ribble, Indianapolis, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 16/421,546

(22) Filed: May 24, 2019

(65) Prior Publication Data

US 2020/0005619 A1  Jan. 2, 2020

Related U.S. Application Data

(60) Provisional application No. 62/696,102, filed on Jul. 10, 2018, provisional application No. 62/691,163, filed on Jun. 28, 2018.

(51) Int. Cl.
    *G08B 21/04*      (2006.01)
    *A61B 5/11*       (2006.01)
    (Continued)

(52) U.S. Cl.
    CPC ........ *G08B 21/0453* (2013.01); *A61B 5/1118* (2013.01); *A61B 5/165* (2013.01);
    (Continued)

(58) Field of Classification Search
    CPC ... G08B 21/0453; A61B 5/024; A61B 5/0816; A61B 5/4266; A61B 5/4803; A61B 5/165
    See application file for complete search history.

(56) References Cited

U.S. PATENT DOCUMENTS 8,140,352 B2   3/2012   Johnson et al.
8,996,428 B2   3/2015   Baras et al.
(Continued)

FOREIGN PATENT DOCUMENTS

WO   WO-2018227282 A1 * 12/2018  ............. G16H 40/20

OTHER PUBLICATIONS

European Search Report dated Jun. 12, 2019; Reference—P/80688. EP01/AF; Application No./Patent No.—19180817.9-1126; Applicant/Proprietor—Hill-Rom Services, Inc.; Title—Methods and Systems for Early Detection of Caregiver Concern About a Care Recipient, Possible Caregiver Impairment, or Both; 14-pages.

*Primary Examiner* — Fekadeselassie Girma
*Assistant Examiner* — Mancil Littlejohn, Jr.
(74) *Attorney, Agent, or Firm* — Barnes & Thornburg LLP

(57) ABSTRACT

A method for detecting the status of a caregiver with respect to one or more patients or detecting possible caregiver impairment includes monitoring an environmental aspect of the patient. The monitored environmental aspect is at least one of caregiver physical activity, caregiver physiological state, and patient surroundings. The method assesses conformance/nonconformance of each monitored aspect relative to a specified norm for that aspect. If the assessment of conformance/nonconformance indicates an intuitive concern of the caregiver or a possible impairment of the caregiver, the method issues a signal to a destination which indicates the possible concern or impairment. A system for carrying out the method includes a sensing subsystem, a processor, and machine readable instructions. The machine readable instructions, when executed by the processor, cause the system to identify, in response to information sensed by the sensing subsystem, the possibility of caregiver concern or impairment.

11 Claims, 13 Drawing Sheets

(51) Int. Cl.
  *A61B 5/00* (2006.01)
  *A61B 5/16* (2006.01)
  A61B 5/024 (2006.01)
  A61B 5/08 (2006.01)

(52) U.S. Cl.
  CPC ............. *A61B 5/746* (2013.01); *A61B 5/024* (2013.01); *A61B 5/0816* (2013.01); *A61B 5/4266* (2013.01); *A61B 5/4803* (2013.01)

(56) References Cited

U.S. PATENT DOCUMENTS

| | | |
|---|---|---|
| 9,355,353 B2 | 5/2016 | Mueller et al. |
| 9,811,992 B1 * | 11/2017 | Neuvirth-Telem ........................... G08B 21/0208 |
| 2012/0041779 A1 | 2/2012 | Borocky et al. |
| 2012/0069131 A1 * | 3/2012 | Abelow ............... G06Q 10/067 348/14.01 |
| 2014/0095181 A1 | 4/2014 | Johnson et al. |
| 2014/0247144 A1 | 9/2014 | Proud |
| 2014/0316813 A1 | 10/2014 | Bauer |
| 2016/0022218 A1 | 1/2016 | Hayes et al. |
| 2016/0239619 A1 | 8/2016 | Abou-Hawili et al. |
| 2018/0158539 A1 | 6/2018 | Gupta et al. |

\* cited by examiner

FIG. 3

| | | Vital Signs Entered | | | | | | | |
|---|---|---|---|---|---|---|---|---|---|
| | 0800 | 0900 | 1000 | 1100 | 1200 | 1300 | 1400 | 1500 | 1600 |
| Pt A | X | | | | X | | | | X |
| Pt B | X | | X | | X | X | | | X |
| Pt C | X | | | | X | | | | X |
| Pt D | X | | | | X | | | | X |
| Pt E | X | | | | X | | | | X |

| PARAMETER (ASPECT) | NORM | ACTUAL (EXAMPLE 1) | ACTUAL (EXAMPLE 2) |
|---|---|---|---|
| VISITS PER DUTY HOUR | 0.5 | 1.1 AS OF 50 MINUTES INTO WORK SHIFT | 0.45 AS OF 6 HRS INTO WORK SHIFT |
| HEART RATE PROFILE | FIG. 4 | CONFORMS TO NORM | CONFORMS TO NORM |
| EQUIPMENT SURVEY | FIG. 6 ITEMS X, Y, Z | CONFORMS TO NORM – NO UNEXPLAINED EQUIPMENT | TWO OCCURRENCES OF EQUIPMENT ITEM B |
| | | POSSIBLE INTUITIVE CONCERN | NO INTUITIVE CONCERN |

FIG. 11

METHODS AND SYSTEMS FOR EARLY DETECTION OF CAREGIVER CONCERN ABOUT A CARE RECIPIENT, POSSIBLE CAREGIVER IMPAIRMENT, OR BOTH

CROSS REFERENCE TO RELATED APPLICATIONS

This application claims priority to the following US Provisional Applications, the contents of which are incorporated herein by reference:

Application 62/691,163 entitled "Detection of Nursing Concerns of Patient Deterioration" filed on Jun. 28, 2018;

Application 62/696,102 entitled "Detection of Nursing Concerns of Patient Deterioration" filed on Jul. 10, 2018.

TECHNICAL FIELD

The subject matter described herein relates to a method for detecting the status of a caregiver with respect to one or more patients or detecting possible caregiver impairment and a system for carrying out the method.

BACKGROUND

Nurses sometimes have a "gut feeling" or "sixth sense" or intuition about a patient's decline in status long before typical objective signs occur (e.g. changes in pulse, respiration, blood pressure, blood oxygen saturation). According to published literature, this intuition can be as effective as objective measures and early warning scores in predicting patient deterioration.

Sometimes a caregiver will begin to change her care practices based on the intuitive concern and will do so even before she herself is consciously aware of any concern and before communicating her concern to others. (In the interest of economy of expression, this specification uses female gender pronouns to refer to caregivers (e.g. nurses) and male gender pronouns to refer to care recipients (e.g. patients).)

If the caregiver were made more consciously aware of her own intuitive concern, such early awareness could cause her to adjust her care practices in ways that may be more useful than if those adjustments are based on a purely intuitive concern. An early alert to the caregiver may also cause her to take advantage of resources that she might otherwise not call on, for example conferring with a more experienced colleague or making sure an item of equipment is on hand.

In addition, if individuals other than the intuitively concerned caregiver were forewarned of her concern those other individuals could then be better prepared to assist the concerned caregiver if the need for assistance arises.

In some cases a caregiver may exhibit atypical physiological signs (e.g. an unusually high heart rate or unusually heavy perspiration) that may or may not be related to an intuitive concern about a patient's health. Even if these signs cannot be attributed to a concern over a patient's health, the fact that the caregiver is exhibiting those signs may reveal that the caregiver is physically or cognitively compromised and therefore may be temporarily incapable of providing high quality care. Knowledge of that fact could be used to guide appropriate intervention.

Accordingly, it is desirable to develop methods and systems which can elevate an intuitive concern and/or the possibility of caregiver impairment to a more conscious level.

SUMMARY

The present invention may comprise one or more of the features recited in the appended claims and/or one or more of the following features or combinations thereof.

A method for detecting the status of a caregiver with respect to one or more patients or detecting possible caregiver impairment includes monitoring an environmental aspect of the patient. The monitored environmental aspect is at least one of A) caregiver physical activity, B) caregiver physiological state; and C) patient surroundings. The method assesses conformance/lack of conformance of each monitored aspect relative to a specified norm for that aspect. If the assessment of conformance/lack of conformance indicates an intuitive concern of the caregiver or a possible impairment of the caregiver, the method issues a signal to a destination. The signal indicates that the caregiver may be concerned about the patient, that the caregiver may be impaired, or both.

A system for detecting the status of a caregiver with respect to one or more patients or detecting possible caregiver impairment includes A) a sensing subsystem, B) a processor, and C) machine readable instructions. The machine readable instructions, when executed by the processor, cause the system to identify, in response to information sensed by the sensing subsystem, that the caregiver may be concerned about a patient, may be impaired, or both.

BRIEF DESCRIPTION OF THE DRAWINGS

The foregoing and other features of the various embodiments of the detection methods and systems described herein will become more apparent from the following detailed description and the accompanying drawings in which:

FIG. 3 is a portion of an example protocol according to which patient vital signs are to be taken every four hours.

FIG. 11 is a table showing more detailed examples of the operation of the system as depicted in FIG. 10.

DETAILED DESCRIPTION

Figure 1A:
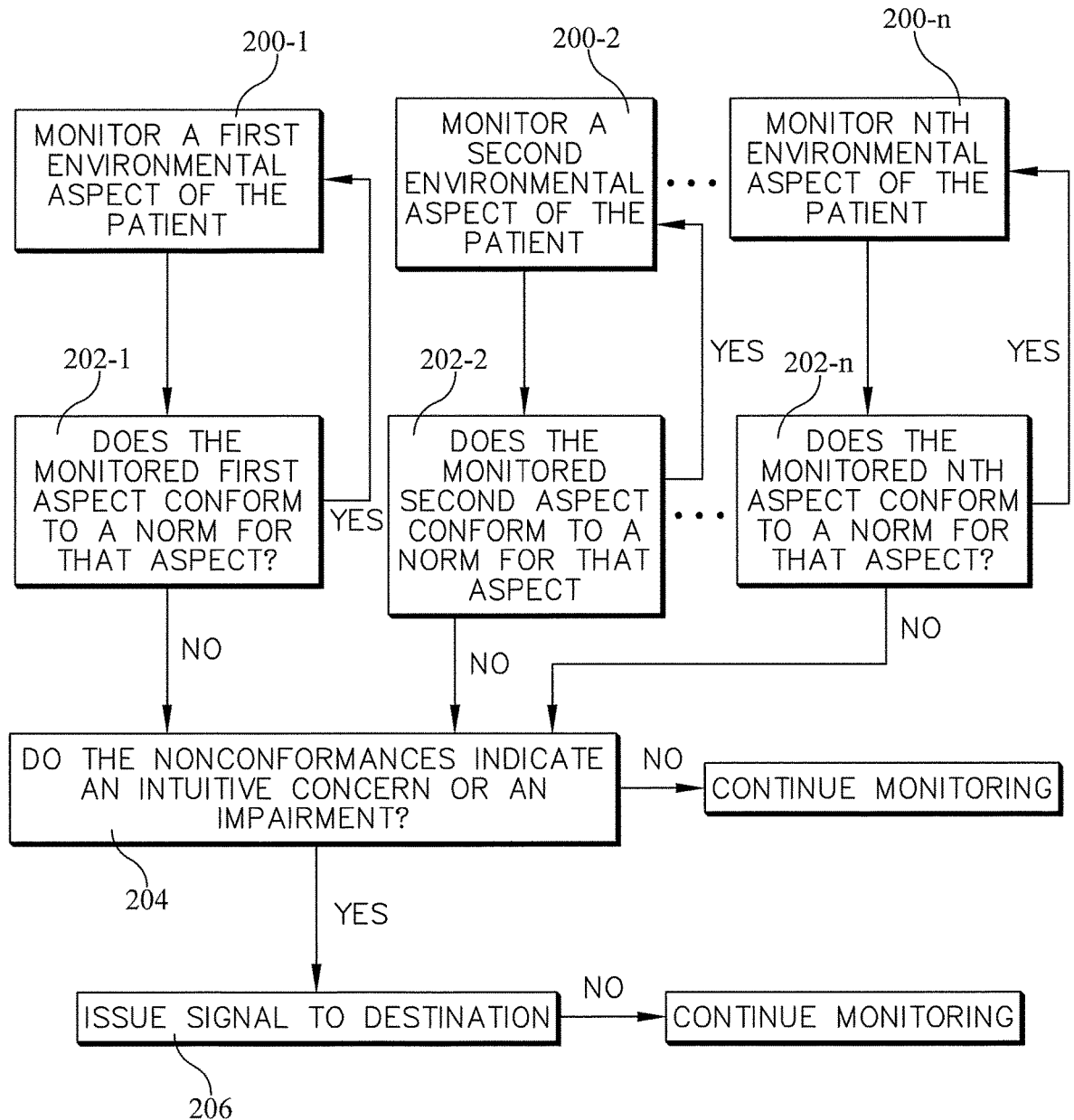
FIG. 1A is a block diagram showing a method for detecting caregiver impairment or the status of a caregiver with respect to a care recipient by monitoring one or more environmental aspects of the care recipient, determining if each monitored aspect conforms to a norm for that aspect, and, if any nonconformances indicate an intuitive concern of the caregiver or indicate that the caregiver is impaired, issuing a signal to a destination.

In this specification and drawings, features similar to or the same as features already described may be identified by reference characters or numerals which are the same as or similar to those previously used. Similar elements may be identified by a common reference character or numeral, with suffixes being used to refer to specific occurrences of the element.

First Method for Early Detection of Caregiver Concern about a Care Recipient, Possible Caregiver Impairment, or Both FIG. 1A is a block diagram showing a method for detecting caregiver impairment or the status of a caregiver with respect to a care recipient. In this specification the caregiver may be referred to as a nurse and the care recipient may be referred to as a patient. One example of a status of a caregiver that is of interest is an intuitive concern that the caregiver has about the patient's medical well being.

Unless specified otherwise, the phrases "medical well being" and "well being" refer to the patient's state of medical health rather than non-medical matters such as dissatisfaction with a meal or unhappiness about aspects of his treatment.

At block 200 the method monitors an environmental aspect of the patient. As used herein, "environmental aspect" refers to a factor external to the patient and includes one or more of A) the behavior or physical activities of the caregiver, B) the caregiver's physiological state, and C) the patient's surroundings, all of which are discussed in more detail below. Because the term "environmental" signifies that the aspects of interest (nurse activity, nurse physiological state, patient's surroundings) are external to the patient, "environmental aspect" does not include aspects of the patient such as his vital signs, appearance, and vocalizations.

At block 202 the method determines whether or not the monitored aspect conforms to a norm for that aspect. (Norms are discussed in more detail below under the heading "Norms and Conformance".) If any of the monitored aspects does not conform to its respective norm, the method advances to block 204 where the method determines if the nonconformances, taken collectively, indicate that the caregiver has an intuitive concern or that the caregiver's abilities might be impaired. If so, the method proceeds to block 206 where it issues a signal to a destination. The signal indicates, based on the monitored environmental aspects and their relationships to their respective norms (conforms to the norm or does not conform to the norm), that the caregiver may have a concern about the patient, and/or that the caregiver's ability to cope with that patient or another patient may be compromised or impaired. The signal may be referred to herein as a "concern signal". The notion of conforming to a norm is referred to herein as "in norm", "within norm" and the like. The notion of not conforming to a norm is referred to herein as "outside the norm", "out of norm" and the like.

FIG. 18 shows a similar method. At blocks 200 the method monitors one or more environmental aspects of the patient. At blocks 202 the method assesses conformance/nonconformance of each aspect to its respective norm. (This specification treats conformance and nonconformance as mutually exclusive outcomes. As a result a negative/positive outcome of a conformance inquiry with respect to an aspect is taken to be a positive/negative outcome of a nonconformance inquiry with respect to that same aspect.) Accounting for both conformances and nonconformances at block 202 reflects the possibility that although some of the aspects may not conform to their norms, those nonconformances may be outweighed by aspects which conform to their norms and will yield an overall determination of conformance to the norms. Similarly, accounting for both conformances and nonconformances reflects the possibility that although some of the aspects may conform to their norms, those conformances may be outweighed by aspects which do not conform to their norms and will yield an overall determination of nonconformance to the norms. If the method determines at block 204 that the conformances and nonconformances indicate an intuitive concern or possible caregiver impairment, the method proceeds to block 206 where it issues a signal to a destination as described in connection with FIG. 1A.

Behavior or Physical Activities of the Caregiver

Figure 2:
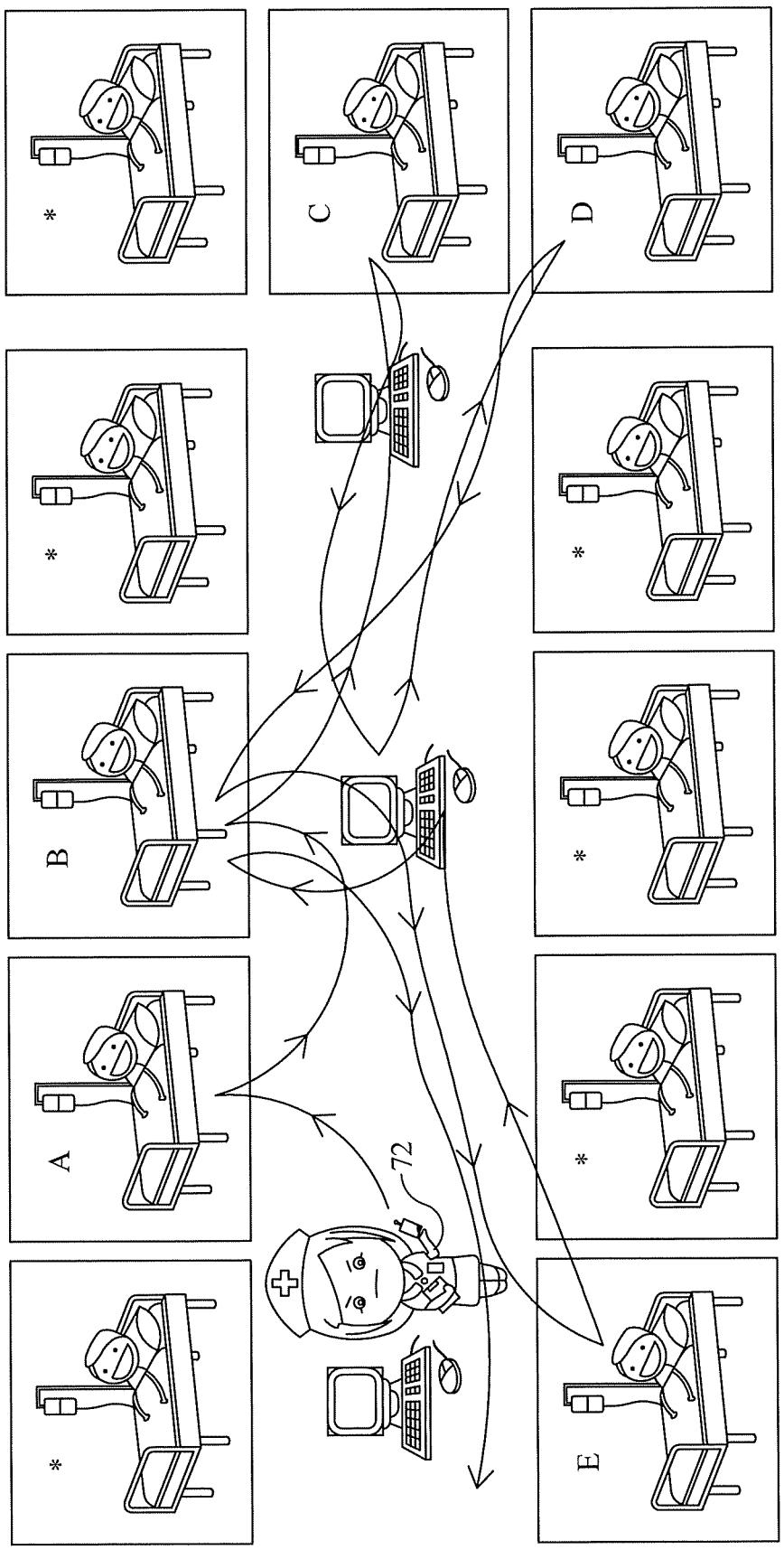
FIG. 2 is a schematic illustration of several rooms in a health care facility, a common area outside the rooms, a set of work stations, a nurse and a line tracing the nurse's movements over a period of time.

FIG. 2 shows one example of a caregiver behavior or physical activity that may indicate that the caregiver has an intuitive concern. FIG. 2 shows eleven rooms in a health care facility, each occupied by a patient in a bed. A common area outside the rooms includes three work stations as indicated by the illustrated computer monitors and mice. The stations are spatially distributed and, as a result, some rooms are closer to a particular work station than are other rooms.

FIG. 2 also shows a nurse. The nurse has primary responsibility for the five patients identified by letters A, B, C, D and E. The nurse has secondary responsibility for the patients in the other rooms, which means that one or more other nurses has primary responsibility for those patients. However the illustrated nurse must nevertheless be vigilant about the well being of those other patients and must be ready to care for them or assist with their care as necessary. Therefore, although patients A, B, C, D and E are the patients referred to in the following example, in principle all eleven patients could have been used in the example.

Over a period of time the nurse visits each patient/patient room, possibly stopping at one of the work stations from time to time, as indicated by the irregular line. During the time period, the nurse has visited patients A, C, D and E once, but has visited patient B three times. If two visits to each patient during the time interval in question is the visitation norm, the frequency with which the nurse has visited patient B, and/or the relative frequency of visitation to patient B in comparison to visitations to the other patients, may be evidence that the nurse has an intuitive but nevertheless valid concern about patient B's well being. This is a specific example of the action at blocks 202 and 204 of FIGS. 1A and 1B where the absolute number of visits or relative visitation rate to patient B within a period of time is compared to a specified visitation norm and found to not conform to the visitation norm.

The duration of a visit (or durations of multiple visits) to a patient also may be evidence that the nurse has an intuitive but valid concern about that patient's well being.

One way to determine whether or not an action of the nurse qualifies as a visit to a given patient is to monitor occurrences of close nurse/patient proximity. For example, close proximity may be gauged by the mere presence of the nurse in the patient's room (particularly if the patient is in a single occupancy room). In another example close proximity is determined by the presence of the nurse within some prescribed distance from the patient's bedside, e.g. within one meter. In another example close proximity is determined by detection of a dialogue between nurse and patient. Whether or not a nurse action qualifies as a visit to a patient may also account for visit duration. For example an occurrence of close nurse proximity to a patient for only a brief time may not qualify as a visit to that patient.

Whether or not an action of the nurse qualifies as a visit to a given patient may depend also on whether there is a reason for the nurse to make visits to the patient or his room which is not related to possible intuitive concerns about the patient's medical well being. For example if a patient issues numerous "nurse calls", the frequency or duration of nurse visits to the patient may not be a good indicator that the nurse has an intuitive concern. In another example a known facility problem (climate control in a specific room not functioning properly) may provoke nurse visits to the room which are related to patient comfort rather than medical well being.

Another example of a caregiver behavior or physical activity that may indicate that the caregiver has an intuitive concern is the location of the caregiver relative to the patient when the location of the caregiver does not qualify as a visit to the patient. Referring again to FIG. 2, the nurse can choose to work at any of the three illustrated work stations. If the time the nurse spends at the center station (just outside patient B's room) exceeds a specified norm, that "out of norm" time expenditure at the center station, in combination with the center station's proximity to patient B's room, may reveal that the nurse has an intuitive concern about patient B. Whether or not the time expenditure is within the norm may account for other factors that might drive the nurse's behavior. Among these are equipment at the other stations being out of service, other stations being in use for lengthy intervals of time by other staff members, and a nurse's known preference to use a particular work station.

Other examples of a caregiver behavior or physical activity that may indicate that the caregiver has an intuitive concern are: 1) the frequency with which the caregiver assesses a vital sign of the patient and/or 2) the count (number or quantity) of vital signs assessed and/or 3) the identity of the vital signs assessed. FIG. 3 shows a protocol according to which patient vital signs are to be taken every four hours, e.g. at 0800 hrs., 1200 hrs., and so forth. In this example the specified norm for the activity in question (vital sign monitoring) is "every four hours" or, alternatively, "at 0800, 01200, 1600, etc." The nurse has complied with the protocol for patients A, C, D and E, but has augmented the protocol for patient B by taking additional readings at 1000 and 1300. The additional readings may indicate that the nurse is intuitively concerned about patient B' medical well being.

With respect to the count of vital signs assessed, if the vital signs monitoring protocol specifies that the patient's heart rate and blood pressure should be checked, but the nurse checks heart rate, blood pressure, respiration rate, and blood oxygen saturation, the nurse's action of having checked two additional vital signs may reveal that the nurse has an intuitive concern about the patient's medical well being.

With respect to the identity of the vital signs assessed, the fact that the nurse checked respiration rate and blood oxygen saturation may reveal, independently of the quantity of vital signs checked (four rather than two), that the nurse has a concern about the patient's medical well being. The specific example of checking respiration and blood oxygen saturation may be an indicator that the nurse is concerned about the patient's respiratory health.

Another example of caregiver behavior or physical activities that may indicate that the caregiver has an intuitive concern about the patient is the frequency with which the caregiver consults the patient's medical record and/or the duration of time the caregiver spends consulting the record and/or the depth of caregiver inquiry into the patient's record. A nurse's intuitive concern may be revealed by a frequency of consultation of the record that exceeds a specified frequency range, and/or time spent consulting the record that exceeds a specified time range and/or the depth of the nurse's inquiry into the record (for example exploring portions of the record that are typically consulted only infrequently).

Another example of a caregiver behavior or physical activity that may indicate that the caregiver has an intuitive concern about the patient is the frequency with which the caregiver consults reference material related to the medical condition of one of her patients and/or the duration of time spent consulting the reference material. For example if patient C is known to have a respiratory condition or a condition which may be a precursor to a respiratory condition, the fact that the nurse consults relevant technical literature or facility protocols relating to respiratory conditions may indicate that the nurse has a concern about the patient's medical well being.

Another example of a caregiver behavior that may indicate that the caregiver has an intuitive concern about the patient is the act of consulting with another individual such as a peer, a more experienced practitioner, a supervisor or a medical specialist. Continuing to use the example of a patient known to have a respiratory condition, the fact that a nurse consults with a respiratory therapist or a pulmonology specialist may be an indicator of a possible intuitive concern about the patient's medical well being.

Consultations may be detected in a number of ways, for example by monitoring face to face or telephone conversations or monitoring the existence of traffic or the content of the traffic on communication media (e.g. text messaging, email). The identities of the individuals involved may also be determined in a number of ways, for example by determining which email accounts are involved in a communication or by using person specific RFID tags or facial recognition to identify individuals.

Caregiver's Physiological State

Another environmental aspect of the patient that may indicate that the caregiver has an intuitive concern about that patient's medical well being is the caregiver's physiological state. In contrast to the behavioral or physical activities described in the "Behavior or Physical Activities of the Caregiver" section of this specification, the caregiver's physiological state is autonomic and relates to the organic processes or functions in an organism (in this case the caregiver) or in any of its parts, including all physical and chemical processes. The fact that a nurse harbors a concern about a patient may affect her stress level. The elevated stress may manifest itself through her physiological signs.

Examples of such signs include heart rate, respiration rate, perspiration, and speech characteristics (e.g. higher than normal voice pitch or speech rate due to autonomic physiological response to stress).

Figure 8:
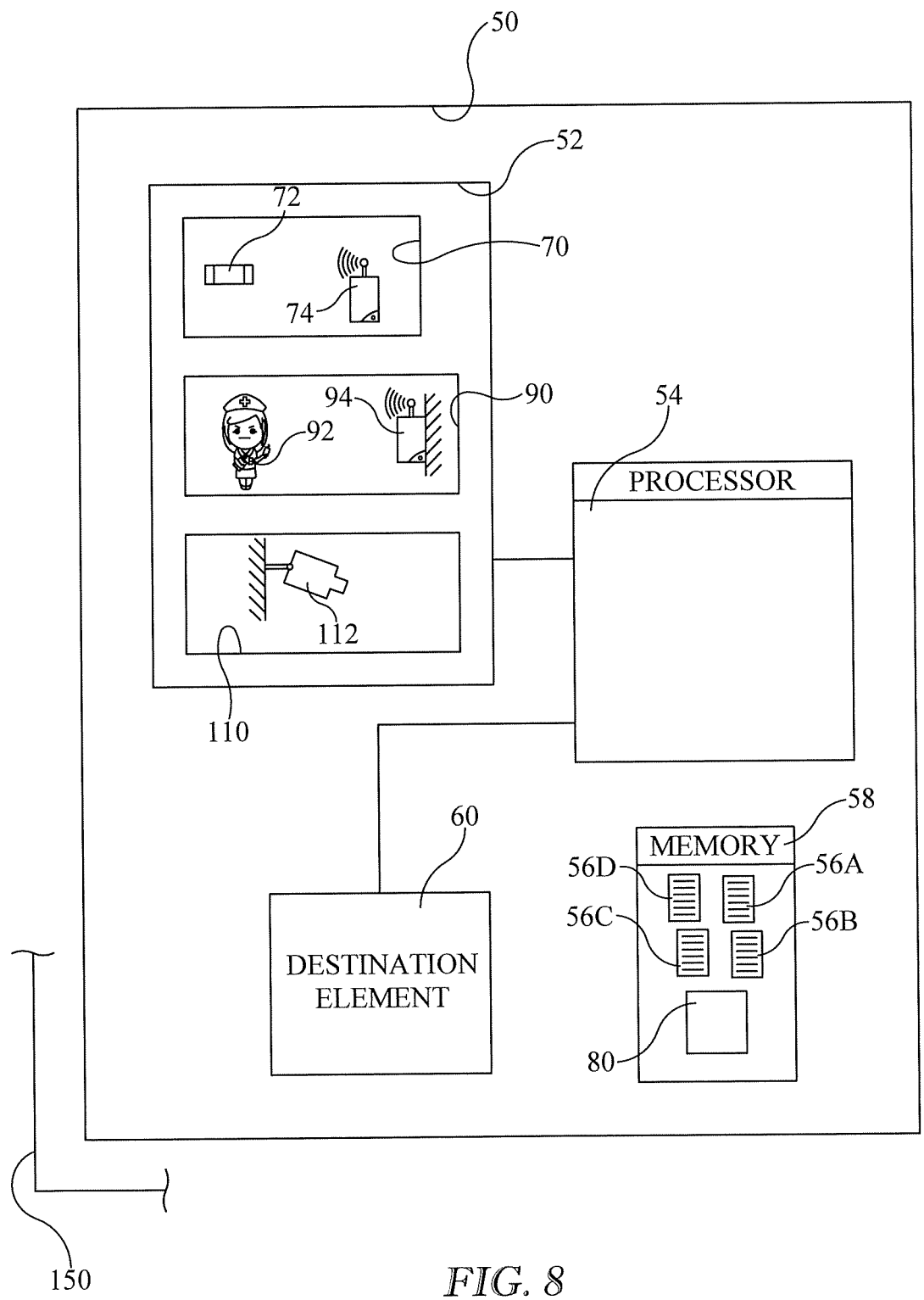
FIG. 8 is a schematic of a system for detecting the status of a caregiver with respect to one or more patients or for detecting possible caregiver impairment and in which the system includes a signal destination.
Figure 9:
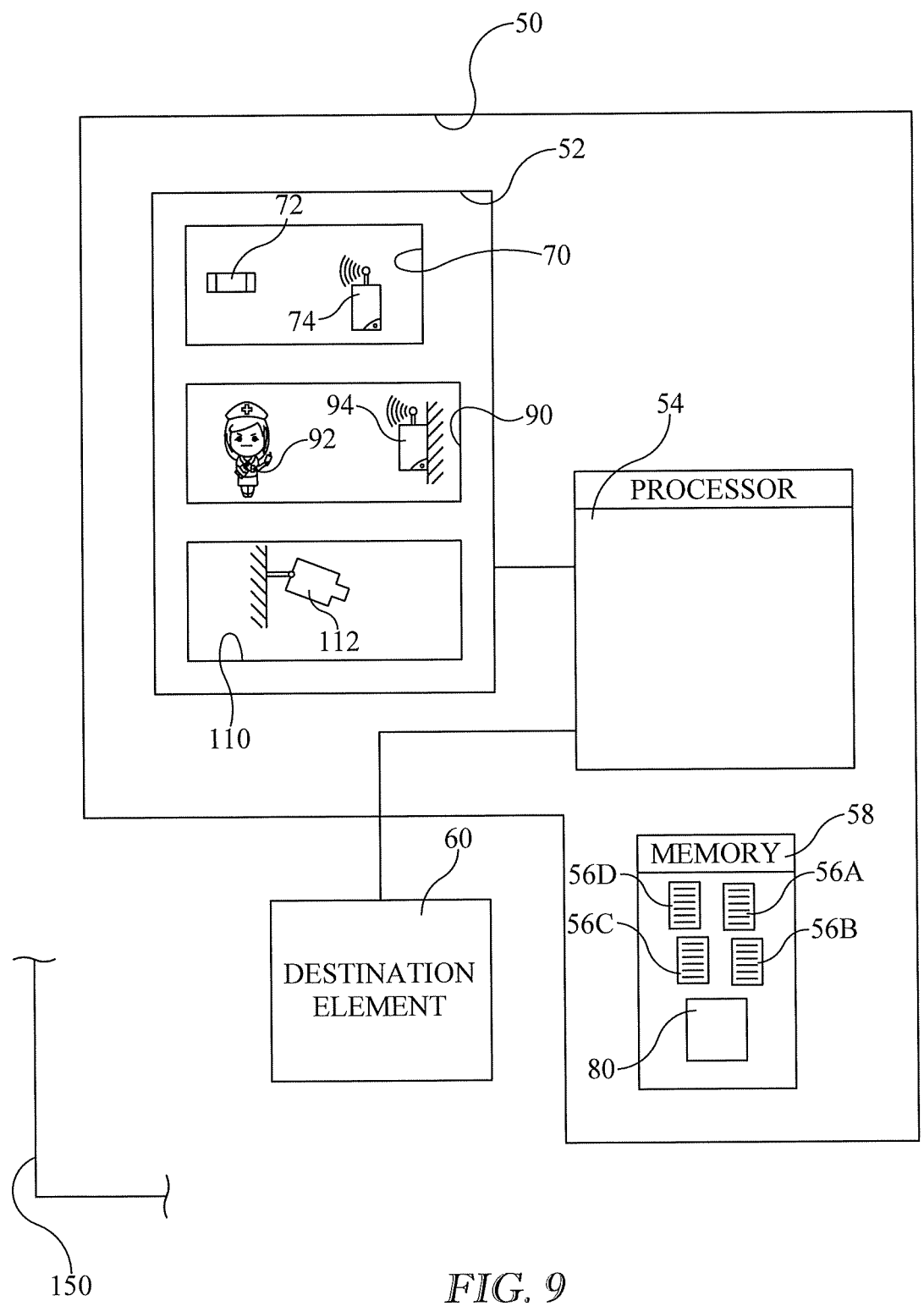
FIG. 9 is a schematic similar to that of FIG. 8 but in which the system does not include the signal destination.

In one embodiment of the method the caregiver's typical or baseline physiological profile is stored, for example in a database 80 (FIGS. 8-9). The profile may be a collection of sub-profiles, one for each physiological parameter of interest. The baseline profile may be determined by monitoring one or more of the caregiver's physiological signs during a number of "calibration" work shifts. The number of calibration work shifts is selected to be high enough that occasional intervals of high stress do not materially affect the overall profile. The sub-profiles obtained from the calibration work shifts are stored and represent the specified norms for the physiological parameters in question. Alternatively, the profile may be a composite or standard profile based on data not specific to the caregiver in question.

Once the profile has been established, the caregiver's physiological readings are monitored during subsequent non-calibration work shifts. Each physiological reading is compared to its specified norm at blocks 202 of FIG. 1A or 1B. Each physiological reading can be considered individually. Additionally or alternatively a physiological reading can be considered in the context of one or more other readings. For example the method can be constructed so that both of two physiological parameters are required to be out of norm as a condition for issuing a concern signal. In another example the ratio of signals may be a useful indicator.

Figure 4:
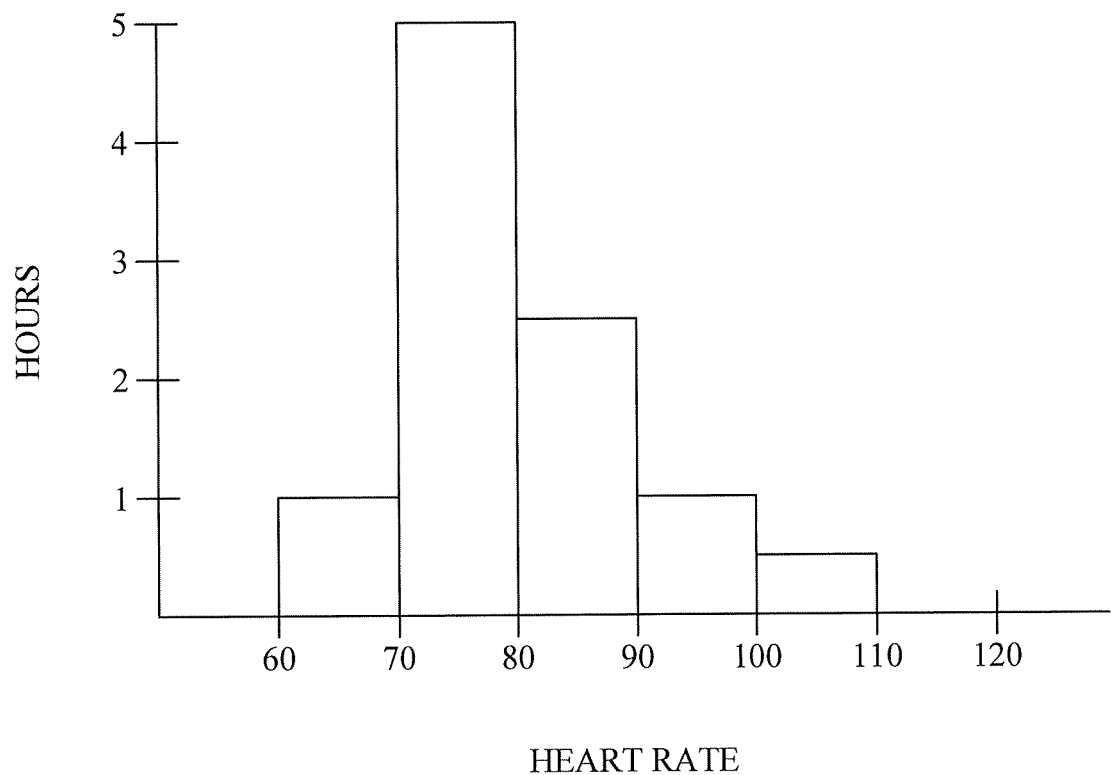
FIG. 4 is a histogram illustrating a caregiver's heart rate profile determined from a number of calibration work shifts.

By way of example, FIG. 4 is a histogram illustrating a caregiver's heart rate profile determined from a number of ten hour calibration work shifts. If it is determined, during a noncalibration shift, that the caregiver's heart rate went out of norm because it had been between 100 and 110 beats per minute (bpm) for more than 30 minutes, the method would issue a concern signal.

Figure 1B:
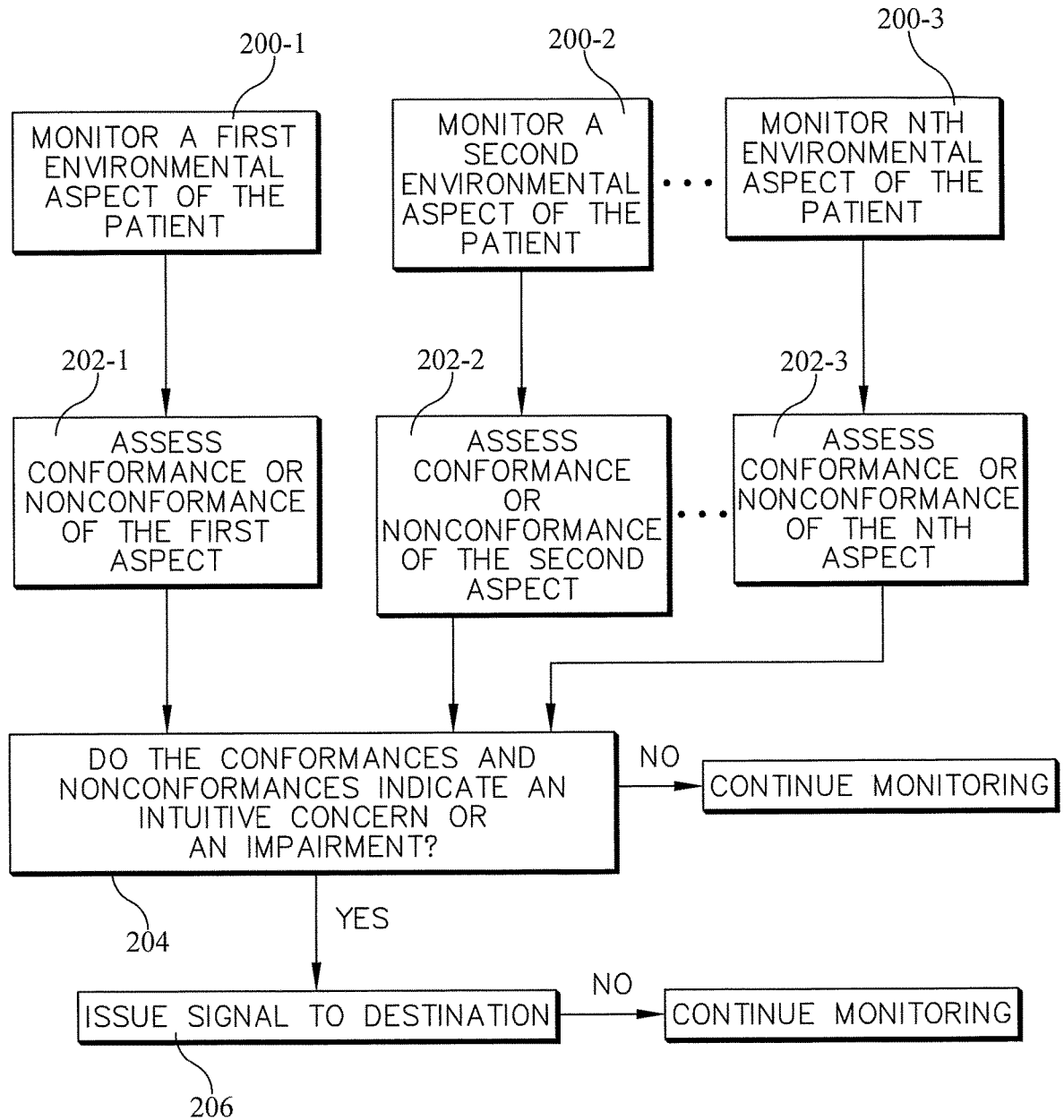
FIG. 1B is a block diagram similar to FIG. 1A showing a similar method in which both conformances and nonconformances are considered.
Figure 5:
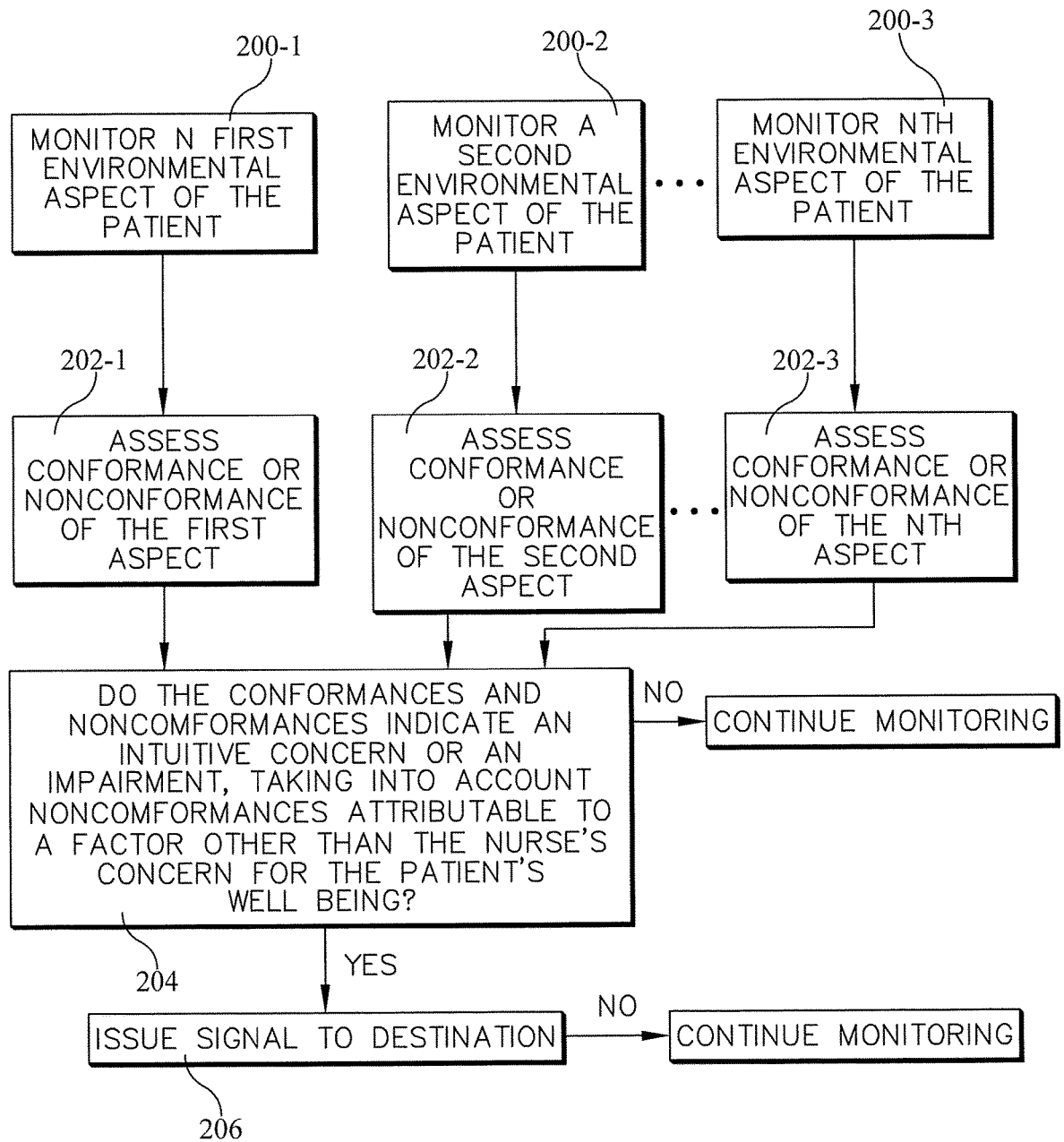
FIG. 5 is a block diagram similar to FIGS. 1A and 1B showing an embodiment of the method in which assessment of the caregiver's physiological state distinguishes between a) physiological measurements which are attributable to the caregiver's role in caring for a particular patient and b) physiological measurements which are not attributable to the caregiver's role in caring for the patient.

FIG. 5 is a block diagram similar to FIGS. 1A and 1B showing an embodiment of the method in which assessment of the caregiver's physiological state distinguishes between a) physiological measurements which are attributable to the caregiver's role in caring for a particular patient and b) physiological measurements which are not attributable to the caregiver's role in caring for the patient, and disregarding the nonattributable measurements. Blocks 200 and 202 are the same as blocks 200 and 202 of FIG. 1B. At block 204 the method determines if the conformances and nonconformances indicate an intuitive concern or an impairment, just as in FIG. 1B. However block 204 of FIG. 5, unlike block 204 of FIG. 1B, also accounts for the possibility that a physiological nonconformance can be explained by some factor other than a nurse's concern for a patient's well being. If the test at block 204 is satisfied, the method advances to block 206 and issues a concern signal as previously described.

As an example of the foregoing, it might be determined that the caregiver's heart rate had been between 80 and 90 bpm for more than the two and a half hours that the profile of FIG. 4 specifies as the norm. However if it is also known that the aggregate patient care workload was especially high during the caregiver's work shift (e.g. more time on the move and attending to patients (heart rate of 70-100 bpm) and less time attending to less strenuous tasks (heart rate of 60-70 bpm)) it may be justified to conclude at block 204 that the deviation from the two and a half hour norm is not attributable to the caregiver's role in caring for and having responsibility for a particular patient. Instead, it is merely the result of overall workload. Accordingly, the method would disregard the nonattributable readings and would follow the NO branch from block 204 back to blocks 200 rather than following the YES branch to block 206.

Alternatively, it may be justifiable to issue a concern signal based on caregiver physiological signs even even if the method does not or cannot distinguish between physiological readings which are attributable to the caregiver's role in caring for the patient and physiological readings which are not so attibutable. Even though there may not be definite evidence that the caregiver has a concern, the out of norm nature of a physiolgical sign or signs may indicate that the caregiver is impaired in some way that could diminish her ability to care for her assigned patients or other patients. The impairment may be a physical impairment such as lack of physical strength due to missing a meal or insufficient water intake, or may be a cognitive impairment such as stress related to a personal problem.

Patient Surroundings

Figure 6:
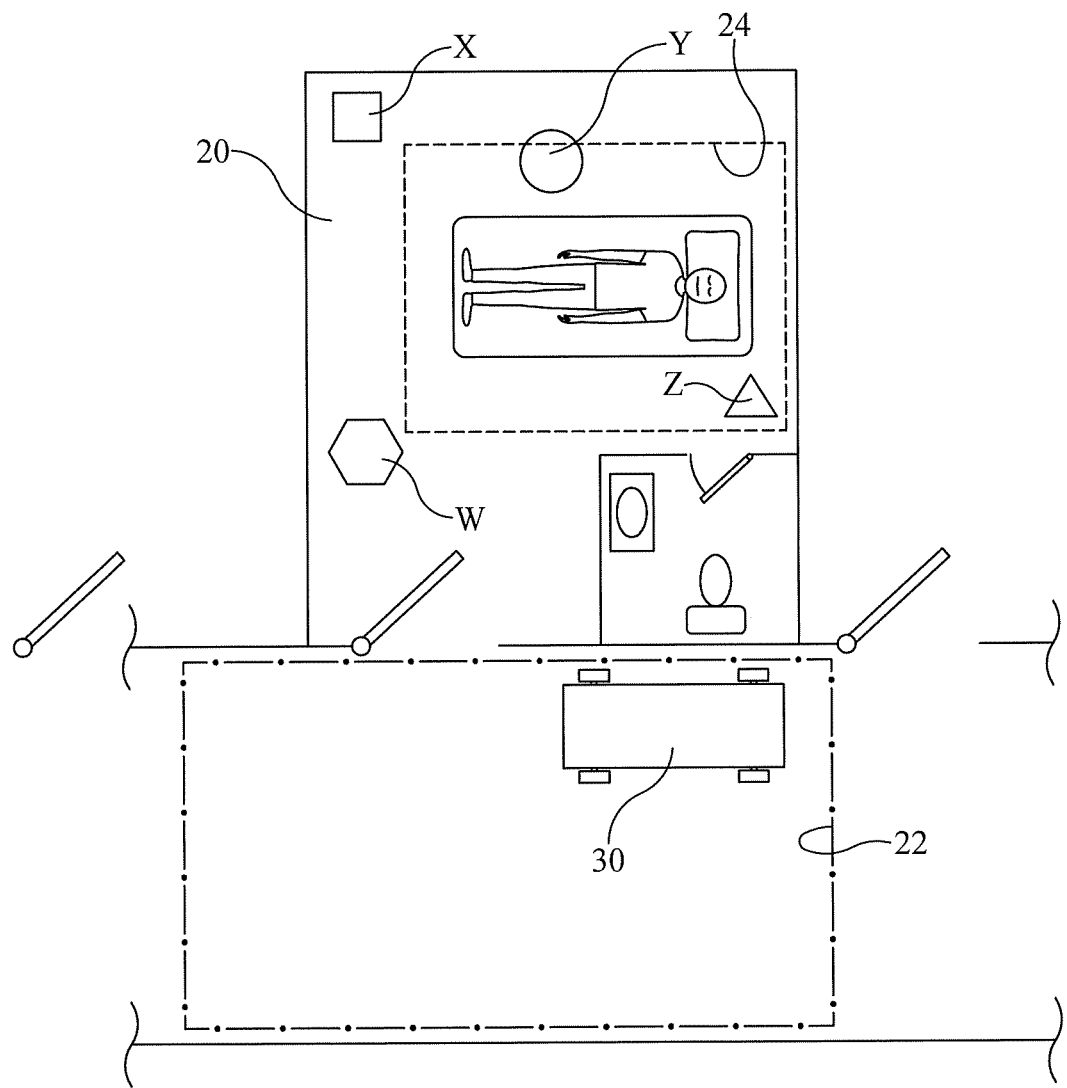
FIG. 6 is a schematic plan view showing a patient and his surroundings in a health care facility.

Referring to FIG. 6, another environmental aspect of the patient that may indicate a caregiver concern about a patient is the patient's surroundings. Examples of surroundings include the patient's room 20, the patient's room in combination with a portion 22 (dash-dot border) of the hallway outside the room, and a prescribed region of space 24 (dashed border) near the bed. The components of the surroundings need not be contiguous. For example regions 22, 24 in combination may be defined as the surroundings even though those regions are noncontiguous.

Figure 7:
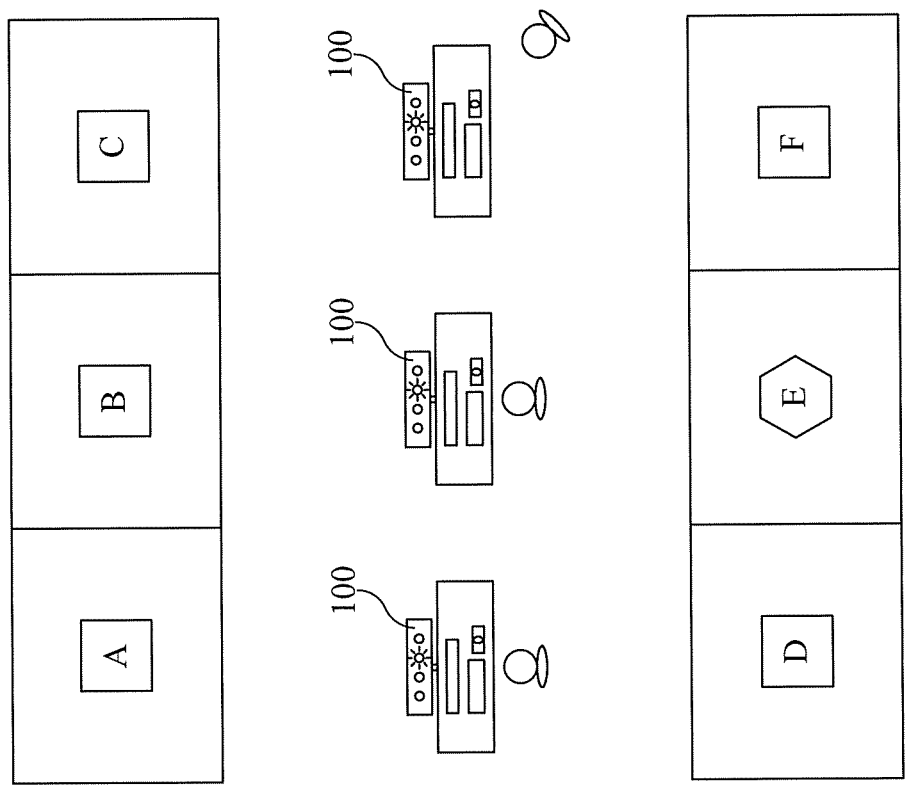
FIG. 7 is a schematic plan view showing several rooms in a health care facility, one of which differs from the others in that it is better suited to providing more advanced care.

In one embodiment the method determines if the surroundings themselves are out of norm. FIG. 7 shows an example in which the nurse has the flexibility to assign the patient to any one of rooms A, B, C, D, E, F. Rooms A, B, C, D, and F are identical or comparable to each other in terms of their suitability for providing care to a patient. Room E differs in that it is better suited than the other rooms for providing more advanced care, for example due to the guaranteed presence of additional items of equipment, telemedicine communication capabilities, etc. If the patient's condition, based on objective measures of his condition, is such that rooms A, B, C, D and F are satisfactory and are available, but the nurse nevertheless places the patient in room E, it may be because the nurse has an intuitive concern about the patient's well being which is not supported by the objective measures. Therefore the surroundings themselves are out of norm in that the use of room E for that patient is not prima facie logical in view of the objective measures.

In another embodiment, assuming the surroundings themselves are within the norm, the method may determine whether or not an out of norm object is present in the surroundings. Taking the patient's room of FIG. 6 as the surroundings, items X, Y and Z are items of equipment present in every room of the facility whereas item W is not. The presence of item W may indicate that the caregiver has a concern which has caused her to pre-position an appropriate additional piece of equipment W in the patient's surroundings. The presence of the additional piece of equipment W may indicate that the nurse has a particular concern about the patient. Moreover the specific nature of the piece of equipment may offer guidance as to the nature of the nurse's concern.

Continuing to refer to FIG. 6, in another example the surroundings include region 22 of the hallway indicated by the dash-dot border. If the standard practice of the facility is to prohibit storage of stretchers in the hallway, the presence of stretcher 30 may reveal that the nurse has pre-positioned it there because of a concern that the patient may need to be transported promptly and with little advance notice to another part of the facility where the matter of concern to the nurse can be more effectively dealt with.

Norms/Conformance to Norms

A norm may be based on empirical information, for example historical data showing that a particular number of visits or a particular relative visitation rate to a single patient is unusually high or that the number of visits or visitation rate to all but one patient is unusually low (suggesting that the nurse is preoccupied, perhaps with a specific patient of concern).

Norms may be nurse specific. Similarly, the determination of whether or not an aspect conforms to a norm which is not nurse specific may itself be nurse specific. For example norms may account for known behavioral characteristics and/or professional qualifications or interests of a caregiver. Using visitations to a patient as an example, a nurse may be known to be especially sympathetic to patients with particular medical conditions (e.g. cardiac patients). Therefore, it might be expected that that nurse would make more visits to a cardiac patient than would be the case for a nurse without that sympathy. In another example a nurse may be known to have a professional interest in and/or special qualifications relating to certain medical conditions (e.g. a wound care specialist). Accordingly, it might be within the norm for that nurse to make more visits to a wound patient even though that same number of visits would be out of norm for a nurse without that interest or qualification.

In the foregoing "known" refers to objective knowledge, for example that a particular nurse specializes in cardiac care. "Known" also includes inferences which might be drawn from nurse activity tracking demonstrating, for example, that a particular nurse has a tendency to visit cardiac patients at an unusually high rate in comparison to her peers.

Norms may also account for the condition of the patient or his location in the facility. Similarly, the determination of whether or not an aspect conforms to a norm which is not patient or patient location specific may itself be patient or patient location specific. For example one or more of the norms for a patient with a medical problem that has not yet been clearly identified may differ from the same norms for a patient with a known medical problem. A patient's location in a facility (e.g. intensive care vs. transition care) may also be a factor in establishing norms. A patient's location in a facility (e.g. intensive care vs. transition care) may also be a factor in determining whether an aspect conforms to or does not conform to a generic norm for that aspect.

In some cases, norm refers to a numerical range, for example the frequency of visits made to the patient or the number of vital signs monitored. In other cases, norm is a non-numerical set of expectations, for example the fact that a nurse consults reference material related to the medical condition of one of her patients or that she inspects portions of the patient's medical record which are usually not reviewed.

The Destination

Returning now to the block diagram of FIG. 1A, when the test at block 204 is satisfied, block 206 issues a signal to a destination. The signal is issued in response to the determination at block 204 that the nurse has a concern about a patient or may be temporarily impaired in her ability to provide care. The destination is any destination which, upon receiving the signal, can render more overt the possibility that the nurse has an intuitive concern or may be impaired.

One example destination for the issued signal is the nurse herself or, as a practical matter, a device associated with the nurse such as a personal communication device that the nurse keeps on her person while on duty. Issuing the signal to the communication device causes the device to present the nurse with a communication advising her of the concern thereby elevating her awareness of its existence.

Another possible destination for the issued signal is a person other than the caregiver or, as a practical matter, a device associated with that other person such as a communication device that the person keeps on her person. Examples of an other person include a peer, a supervisor, a person with more experience or a person with specialized knowledge or skills which can be brought to bear on the concern (provided the nature of the concern has been identified). Issuing the signal to the communication device causes the device to present the person with a communication advising her of the nurse's concern. The other person can then approach the nurse in question for a discussion.

Another possible destination for the issued signal is an information repository such as a memory of a facility information network. Issuing the signal to the information repository can cause the information network associated with the repository to notify, for example, supervisory members of the staff. A member of the supervisory staff can then intervene to establish whether or not a valid concern actually exists and to take appropriate action.

Another possible destination for the issued signal is an annunciator 100 (FIG. 7) for example a light or buzzer at a nurse's station which indicates a possible concern on the part of the nurse in question or that the nurse's physiological signs suggest the possibility of an impairment to her caregiving abilities. Issuing the signal to the annunciator can inform others of the possible concern or impairment so that they can intervene.

In view of recent advances in robotics, artificial intelligence, and machine learning, another possible destination is a robot, possibly one programmed with Azimov's three laws of robotics.

The Issued Signal

The signal issued at block 206 may be a signal which is adapted, either by its information content or the destination to which it is routed, to place human and nonhuman resources in at least a standby status. Placing resources in standby status may be especially justified if the nature of the concern can be identified. For example if the signal was issued, at least in part, because the nurse was determined to have been making inquiries into reference materials about a particular medical condition, staff members with more experience and/or expertise in dealing with that condition could then be alerted, thus placing those individuals on standby status. Specialty equipment that the staff members may need in order to deal with the identified condition can also be placed on standby status to signal to other individuals that the equipment is temporarily reserved to address the possible concern. Placing equipment on standby status can be carried out by enforcing a protocol requiring nurses to access the facility information network and "check out" the specialty equipment. When that equipment needs to be held in reserve for the reasons described above, processor 54 can show the status of the equipment as "RESERVED". Another embodiment of the method goes beyond placing personnel and equipment on standby status and instead deploys the personnel and orders deployment of any specialty equipment.

In another variant of the method, the signal issued at block 206 of FIGS. 1A and 1B can also be used as a signal to re-prioritize communications to the nurse. As an example, the indication of a possible concern about a patient, or the possibility that the nurse's abilities are impaired, could cause re-prioritization of messages to the nurse's personal communication device. For example a message to the personal communication device intended to elevate her awareness of a concern which she has not yet consciously recognized may be given a higher priority than a message reminding her of a staff meeting to take place in ten minutes.

The concern signal has been described as a signal which indicates that the caregiver may be concerned about the patient, that the caregiver may be impaired, or both. The system may also produce a no-concern signal to indicate that no caregiver impairment or concern about the patient has been detected. Alternatively, an indication of no concern can take the form of the absence of a concern signal. An absent signal can be thought of as a null signal.

First System for Early Detection of Caregiver Concern about a Care Recipient, Possible Caregiver Impairment, or Both FIG. 8 shows a system 50 for detecting the status of a caregiver with respect to one or more patients or detecting possible caregiver impairment. The system may be part of a more comprehensive information technology (IT) network 150. System 50 comprises a sensing subsystem 52 a processor 54, and machine readable instructions 56 stored in a memory 58. The memory also includes a data repository 80. The memory itself can be considered part of system 50 or can be an element external to system 50. The instructions 56 are readable and executable by processor 54. When executed by the processor, instructions 56 cause system 50 to identify, in response to information sensed by sensing subsystem 52, that a caregiver is concerned about a patient, impaired in her ability to adequately care for the patient, or both. The instructions may include algorithms for evaluating conformances and nonconformances, object and facial recognition instructions, and machine learning instructions. The system as illustrated in FIG. 8 also includes a destination element 60. The sensing subsystem and destination element are discussed in more detail below. As will become apparent the sensing subsystem is comprised of sub-subsystems, however these are referred to a simply subsystems.

Sensing Subsystem/Asset Tracking Subsystem

Illustrated sensing subsystem 50 includes an asset tracking subsystem 70 adapted to track and/or locate human and/or nonhuman assets. With no intent to limit this disclosure and accompanying claims to any specific embodiment, one example of a locating and/or tracking subsystem is the CenTrak Enterprise Location Services' system. Additional information about the CenTrak system may be found at https://www.centrak.com/. Also without intent to limit the description or claims the system will be referred to herein as a "real time locating system" (RTLS).

One embodiment of a RTLS includes radio frequency identification (RFID) tags 72 and an RFID reader or readers 74. The tags may be attached to objects so that each tag is associated with a specific object or a type of object (e.g. IV pole, tracheostomy kit). Tags may also be uniquely associated with nurses, for example by being attached to a nurse's clothing as illustrated in FIG. 2 by RFID tag 72 affixed to the nurse's uniform). The RFID readers are located within communication range of any place the tagged objects or personnel might reasonably be found. Taking a hospital as an example, the readers may be positioned to detect objects and personnel inside the hospital but not outside the hospital.

The RTLS, in response to machine readable instructions such as instructions 56, may be used to surveil activities of the nurse which are discernible from information provided by the RTLS. As noted in the "Behavior or Physical Activities of the Caregiver" section of this specification, these include activities related to frequency and duration of visitations to the patient, and the location of the caregiver relative to the patient when the location of the caregiver does not qualify as a visit to the patient. The reader is referred to the "Behavior or Physical Activities of the Caregiver" section of this specification for a more in depth discussion.

Sensing Subsystem/Physiological Monitoring Subsystem

Illustrated sensing subsystem 50 also includes a physiological monitoring subsystem 90. In one example the physiological monitoring system includes one or more physiological sensors 92 associated with each nurse or other caregiver of interest and a receiver 94 adapted to receive signals from the sensor 92 and convey the sensed information to processor 54. The receivers are located within communication range of any place the nurse might reasonably be found. Taking a hospital as an example, the receivers may be positioned to receive signals from sensors as long as the individuals being tracked are inside the hospital but not when they are outside the hospital.

As described in the "Caregiver's Physiological State" section of this specification, data from the physiological sensors is monitored during the nurse's non-calibration work shifts. Processor 54, acting in accordance with machine readable instructions 56, compares the physiological readings to the norms established for that nurse during calibration work shifts and determines whether the readings are within the norm or out of norm. The reader is referred to the "Caregiver's Physiological State" section of this specification for a more in depth discussion.

Sensing Subsystem/Surroundings Monitoring Subsystem

Illustrated sensing subsystem 50 may also include a surroundings recognition or surroundings monitoring subsystem 110. In one example the surroundings recognition subsystem includes a camera 112 sensitive to wavelengths appropriate to its monitoring task. Such wavelengths may include visible and infrared wavelengths. The surroundings recognition subsystem also includes appropriate machine readable and executable instructions. The instructions may include object recognition software/instructions.

As described in the "Patient Surroundings" section of this specification, processor 54, acting in accordance with machine readable instructions 56, uses information from the camera to determine whether or not an out of norm object is present in the surroundings. The reader is referred to the "Patient Surroundings" section of this specification for a more in depth discussion.

As also described in the "Patient Surroundings" section of this specification, the processor, acting in accordance with machine readable instructions 56, may also determine if the patient's surroundings as a whole (i.e. the room itself) is out of norm. In one embodiment the processor uses information from asset tracking subsystem 70 to determine that the nurse has placed a particular patient in a particular room. If the room is suitable for advanced care which is not prima facie required for the patient in question, the processor, in response to instructions 56, determines that the room itself is out of norm. The reader is again referred to the "Patient Surroundings" section of this specification for a more in depth discussion.

As explained under the "Behavior or Physical Activities of the Caregiver" heading of this specification the frequency with which the caregiver takes readings of a vital sign of the patient and/or 2) the count (number or quantity) of vital signs assessed and/or 3) the identity of the vital signs assessed may indicate that the caregiver has an intuitive concern. One way that system 50 may compile these statistics is by executing instructions 56 that monitor the nurse's vital signs entries into the particular patient's medical record. Another way that system 50 may compile these statistics is by executing instructions 56 which monitor usage of the equipment used to take vital signs measurements and correlate that usage to nurse/patient proximity as revealed by the asset tracking subsystem 70 and/or surroundings recognition subsystem 110.

As explained under the "Behavior or Physical Activities of the Caregiver" heading of this specification the frequency with which the caregiver consults reference material related to the medical condition of one of her patients and/or the duration of time spent consulting the reference material may indicate that the caregiver has an intuitive concern. One way that system 50 may compile these statistics is by executing instructions 56 that monitor the nurse's inquiries into records stored in database 80.

The immediately preceeding discussion associates the asset tracking subsystem, the physiological monitoring subsystem, and the surroundings recognition subsystem with specific tasks. However not all of the subsystems are necessarily required, although a nonrequired subsystem may nevertheless be included to provide redundancy. Moreover, some tasks can be allocated to a subsystem other than the subsystem associated with the task in the above description.

One subsystem which may not be required is the asset tracking subsystem 70. Instead, it may be possible to use the surroundings recognition subsystem 110 to identify both objects (e.g. by way of object recognition software/instructions) and nurses (via facial recognition software/instructions).

To the extent that the physiological monitoring subsystem 90 can determine the location of a nurse, it may be possible to use the asset tracking subsystem 70 to monitor only objects rather than both objects and people. Or, the asset tracking subsystem can be dispensed with by assigning its nurse locating task to the physiological monitoring subsystem 90 as just described and assigning its object locating and tracking task to the surroundings recognition subsystem 110.

In general, to the extent that subsystems 70, 90, 110 have overlapping or duplicate capabilities it may be necessary to employ only a subset of those subsystems and/or to employ less than all of the functionality of one or more of subsystems 90, 100, 110.

Destination Element

The destination element 60 of FIG. 8 corresponds to the various destinations described above in connection with the method for detecting the status of a caregiver with respect to one or more patients or detecting possible caregiver impairment. Therefore, the destination element may be one or more of A) an information repository, B) the caregiver or a device associated with the caregiver, C) a person other than the caregiver or a device associated with the person other than the caregiver, D) a robot, and E) an annunciator signaling device.

FIG. 9 is a system diagram similar to that of FIG. 8, however in FIG. 9 destination element 60 is not considered to be an element of system 50.

The system and method described in this specification accounts for caregiver physical activity, caregiver physiological state, and patient surroundings. However a system and/or method for early detection of nurse concerns and/or nurse impairment may not require consideration of all of those aspects. In other words the method and/or system may need to account for only one or any two of those aspects.

Figure 10:
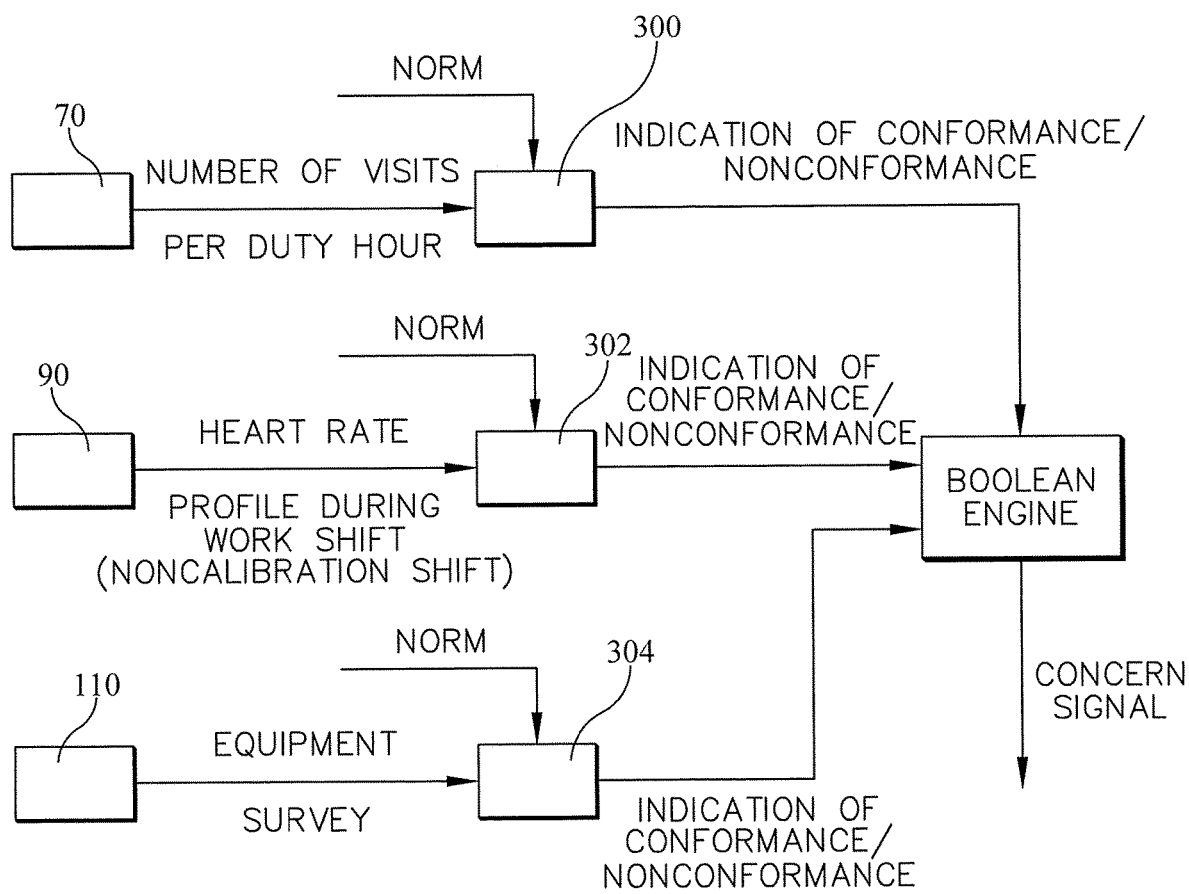
FIG. 10 is a flow chart showing a simple example of the functioning of the system of FIG. 8 or FIG. 9 in response to executing machine readable instructions.

FIG. 10 is a flow chart showing a simple example of the functioning of system 50 in response to executing the machine readable instructions. Blocks 70, 90, and 110 are the asset tracking subsystem, physiological monitoring subsystem, and surroundings recognition subsystem previously described. In the example, asset tracking subsystem 70 reports, for a particular nurse, the number of visits she has made to a particular patient; physiological monitoring subsystem 90 reports her heart rate profile; surroundings recognition subsystem 110 reports the results of an equipment survey in the patient's room. Each reported aspect is compared to its norm at blocks 300, 302, 304. Each block outputs an indication of conformance/nonconformance. The conformance/nonconformance assessments are evaluated by the machine readable instructions 56, which are represented in FIG. 10 as a "Boolean Engine". Based on the evaluation, the Boolean engine generates (or does not generate) a concern signal.

FIG. 11 is a table showing more detailed examples of the operation of the system as depicted in FIG. 10. The first (leftmost) column lists example aspects of interest. The second column shows an example norm for each aspect. The third and fourth columns show two examples of assessing conformance/nonconformance. In example 1 the Boolean Engine has determined that the high rate of visits to the patient justifies the determination that the nurse has an intuitive concern. In example 2 the visitation rate is in close conformance to the norm, and the nurse's heart rate profile is in conformance to its norm. The equipment survey reveals that the patient's room contains two of equipment item B, not just one as specified by the profile. However the logic of the Boolean Engine is set up to not regard duplicate items of equipment as a nonconformance, or at least to regard the duplication as a nonconformance which, without more, does not justify a determination that the nurse has an intuitive concern. Accordingly, a concern signal is not issued.

The foregoing examples illustrate that the exact formula for declaring that a set of conformances/noncomformances indicates an intuitive concern or a nurse impairment is, at least to some extent, a matter of judgement to be exercised during design of the system. The examples also illustrate that the designer can apply tolerances to the conformance/nonconformance thresholds. The example in FIG. 11 is that the slight shortfall of visitations (0.45 vs. 0.5 at six hours into the work shift) was not considered to be meaningful.

The section headings in this specification refer to the above described method as a "First Method . . . ", and refer to the above described system as a "First System . . . " to indicate that variations to the method and system are within the scope of the existing description. For example, the described method and system account for A) caregiver physical activity, B) caregiver physiological state; and C) patient surroundings. However methods and systems which account for only a subset of those environmental aspects, for example those enumerated with a dot in table 1 below, are also within the scope of this disclosure.

TABLE 1

| Aspect Accounted For | | |
|---|---|---|
| CAREGIVER PHYSICAL ACTIVITY | CAREGIVER PHYSIOLOGICAL STATE | PATIENT SURROUNDINGS |
| • | • | • |
| • | • | |
| • | | • |
| • | | |
| | • | |
| | | • |

Figure 12:
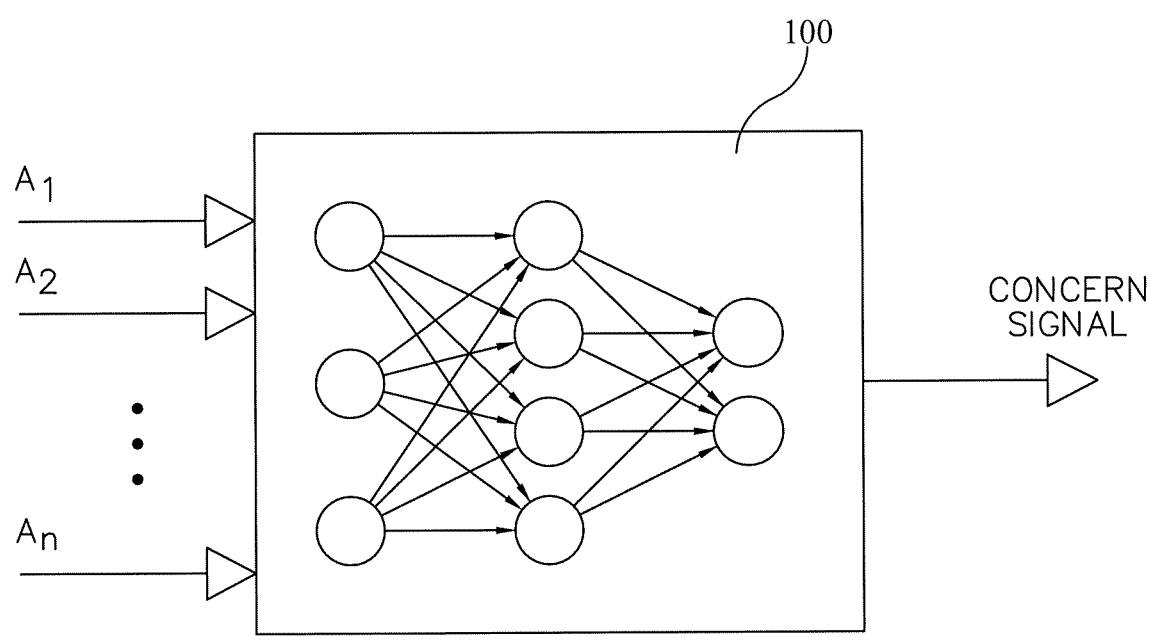
FIG. 12 is a block diagram of an embodiment which uses a machine learning algorithm, such as a neural network, to determine if a caregiver has an intuitive concern about a patient's medical well-being.

FIG. 12 is a block diagram of an embodiment which uses a machine learning algorithm, such as a neural network 400, to determine if a caregiver has an intuitive concern about a patient's medical well-being. Inputs to the illustrated neural network include the environmental aspects $A_1, A_2, \ldots A_n$ of the patient. The neural network produces a concern signal in response to the operation of the neural network.

Although this disclosure refers to specific embodiments, it will be understood by those skilled in the art that various changes in form and detail may be made without departing from the subject matter set forth in the accompanying claims.

We claim:

1. A method for detecting the status of a caregiver with respect to one or more patients or detecting possible caregiver impairment comprising:
   monitoring an environmental aspect of the patient, the environmental aspect including:
   A) caregiver physical activity including frequency with which the caregiver consults the patient's medical record and duration of time the caregiver spends consulting the patient's medical record and depth of caregiver inquiry into the patient's medical record:
   the environmental aspect also including at least one of:
   B) caregiver physiological state; and
   C) patient surroundings;
   assessing conformance/nonconformance of each monitored aspect relative to a specified norm for that aspect; and
   in response to the step of assessing conformance/nonconformance indicating an intuitive concern of the caregiver or a possible impairment of the caregiver, issuing a signal to a destination, the signal indicating at least one of:
   a) a caregiver concern about the patient, and
   b) a caregiver impairment.

2. The method of claim 1 wherein the monitored caregiver physical activity includes at least one of:
   A1) frequency and/or duration of caregiver visits to the patient;
   A2) location of the caregiver relative to the patient;
   A3) frequency with which the caregiver assesses a vital sign of the patient and/or count of vital signs assessed, and/or identity of vital signs assessed; and
   A4) frequency with which the caregiver consults reference material and/or duration of time spent consulting the reference material, the reference material being related to the medical condition of the patient.

3. The method of claim 1 wherein the step of determining whether or not the caregiver's physiological state conforms to a norm includes distinguishing between a) physiological measurements which are attributable to the caregiver's role in caring for the patient and b) physiological measurements which are not attributable to the caregiver's role in caring for the patient, and disregarding the nonattributable measurements.

4. The method of claim 1 wherein the step of determining whether or not the patient's surroundings conform to a specified norm includes at least one of:
   determining when the surroundings are out of norm; and
   when the surroundings are within norm, determining when an out of norm object is present in the surroundings.

5. The method of claim 1 wherein the step of issuing a signal comprises issuing a signal to at least one of:
   A) an information repository,
   B) the caregiver or a device associated with the caregiver,
   C) a person other than the caregiver or a device associated with the person other than the caregiver,
   D) a robot, and
   E) an annunciator.

6. The method of claim 1 including the step of:
   if the step of assessing conformance/nonconformance indicates an intuitive concern of the caregiver or a possible impairment of the caregiver:
   a) determining if priority of communications involving the caregiver and/or patient should be adjusted; and
   b) if it is determined that priority of communications involving the caregiver and/or patient should be adjusted, carrying out the adjustment.

7. The method of claim 1 wherein the issued signal is adapted, at least in part, to place human and nonhuman resources in at least a standby status.

8. A system for detecting the status of a caregiver with respect to one or more patients or detecting possible caregiver impairment, the system comprising:
   A) a sensing subsystem;
   B) a processor; and
   C) machine readable instructions which, when executed by the processor, cause the system to implement the method of claim 1.

9. The system of claim 8 wherein the system:
   A) includes a destination element, and
   B) wherein in response to the identification that the caregiver is at least one of
   a) concerned about the patient and
   b) impaired, the system communicates the identification of concern or impairment to the destination element.

10. The system of claim 9 wherein the destination element is at least one of:
    A) an information repository;
    B) the caregiver or a device associated with the caregiver;
    C) a person other than the caregiver or a device associated with the person other than the caregiver;
    D) a robot; and
    E) an annunciator.

11. The system of claim 8 wherein the sensing subsystem includes one or more of:
    a) an asset tracking subsystem;
    b) a physiological monitoring subsystem; and
    c) a surroundings recognition subsystem.

* * * * *